(12) United States Patent
Johnson

(10) Patent No.: US 11,154,415 B2
(45) Date of Patent: Oct. 26, 2021

(54) OSTOMY LEAK PROOF PROTECTION BAG

(71) Applicant: Althia Johnson, Bronx, NY (US)

(72) Inventor: Althia Johnson, Bronx, NY (US)

( * ) Notice: Subject to any disclaimer, the term of this patent is extended or adjusted under 35 U.S.C. 154(b) by 851 days.

(21) Appl. No.: 15/678,267

(22) Filed: Aug. 16, 2017

(65) Prior Publication Data

US 2018/0049909 A1    Feb. 22, 2018

Related U.S. Application Data

(60) Provisional application No. 62/375,550, filed on Aug. 16, 2016.

(51) Int. Cl.
*A61F 5/44* (2006.01)
*A61F 5/443* (2006.01)
*A61F 5/445* (2006.01)

(52) U.S. Cl.
CPC ............ *A61F 5/4404* (2013.01); *A61F 5/443* (2013.01); *A61F 5/445* (2013.01)

(58) Field of Classification Search
CPC combination set(s) only.
See application file for complete search history.

(56) References Cited

U.S. PATENT DOCUMENTS

| | | | | |
|---|---|---|---|---|
| 3,089,493 A * | 5/1963 | Galindo | A61F 5/445 | 604/342 |
| 4,403,991 A * | 9/1983 | Hill | A61F 5/443 | 604/337 |
| 4,755,177 A * | 7/1988 | Hill | A61F 5/443 | 604/336 |
| 5,417,677 A * | 5/1995 | Schneider | A61F 5/445 | 604/332 |
| 5,423,782 A * | 6/1995 | Wolrich | A61F 5/445 | 604/339 |
| 5,591,144 A * | 1/1997 | Smith | A61F 5/445 | 604/327 |
| 5,769,831 A * | 6/1998 | Freeman | A61F 5/445 | 604/332 |
| 5,785,695 A * | 7/1998 | Sato | A61F 5/448 | 604/338 |
| 5,865,819 A * | 2/1999 | Cisko, Jr. | A61F 5/445 | 604/339 |
| 5,938,647 A * | 8/1999 | Smith | A61F 5/445 | 604/332 |
| 7,179,245 B2 * | 2/2007 | Giori | A61F 5/448 | 604/332 |

(Continued)

*Primary Examiner* — Guy K Townsend
(74) *Attorney, Agent, or Firm* — Jones Day

(57) ABSTRACT

An ostomy bag system includes an ostomy bag having an ostomy bag adhesive and an ostomy bag pouch, and an ostomy leak proof protection bag having a cover adhesive and a cover pouch. The cover adhesive may enclose the ostomy bag adhesive and the cover pouch may enclose the ostomy bag pouch for additional sealing and protection. A method of using the ostomy bag system includes securing an ostomy bag adhesive to a patient's body, securing a cover adhesive enclosing the ostomy bag adhesive to another position on the patient's body, and removing the ostomy bag system in a single step after use of the ostomy bag system. In another example, the ostomy leak proof protection bag may further include a hinge on the cover adhesive to allow access to the ostomy bag without removal of the ostomy leak proof protection bag.

14 Claims, 6 Drawing Sheets

(56) References Cited

U.S. PATENT DOCUMENTS

| | | | | |
|---|---|---|---|---|
| 7,214,217 B2* | 5/2007 | Pedersen | .................. | A61F 5/441 |
| | | | | 604/332 |
| 8,118,797 B2* | 2/2012 | Giori | ................... | A61L 28/0069 |
| | | | | 604/332 |
| 8,343,121 B2* | 1/2013 | Cramer | ................... | A61F 5/445 |
| | | | | 604/344 |
| 8,740,832 B2* | 6/2014 | Smith | ..................... | A61F 5/445 |
| | | | | 604/8 |
| 9,498,372 B2* | 11/2016 | Fattman | .................. | A61F 5/443 |
| | | | | 604/344 |
| 10,022,260 B2* | 7/2018 | Richmann | ............... | A61F 5/445 |
| | | | | 604/344 |
| 10,105,255 B2* | 10/2018 | Fattman | .................. | A61F 5/448 |
| | | | | 604/344 |
| 2004/0059306 A1* | 3/2004 | Tsai | ........................ | A61F 5/445 |
| | | | | 604/332 |
| 2005/0084634 A1* | 4/2005 | Giori | ........................ | B32B 9/04 |
| | | | | 428/35.2 |
| 2005/0113770 A1* | 5/2005 | Pedersen | .................. | B32B 1/02 |
| | | | | 604/332 |
| 2010/0114045 A1* | 5/2010 | Cramer | ................... | A61F 5/445 |
| | | | | 604/338 |
| 2011/0213321 A1* | 9/2011 | Fattman | .................. | A61F 5/448 |
| | | | | 604/344 |
| 2011/0238024 A1* | 9/2011 | Smith | ..................... | A61F 5/445 |
| | | | | 604/336 |
| 2013/0253455 A1* | 9/2013 | Masters | .................. | A61F 5/445 |
| | | | | 604/332 |
| 2015/0209172 A1* | 7/2015 | Richmann | ............... | A61F 5/445 |
| | | | | 604/332 |

* cited by examiner

OSTOMY LEAK PROOF PROTECTION BAG

CROSS-REFERENCE TO RELATED APPLICATIONS

This application claims the benefit of priority to U.S. Provisional Patent Application No. 62/375,550, filed Aug. 16, 2016, which is herein incorporated by reference in its entirety for all purposes.

STATEMENT REGARDING FEDERALLY SPONSORED RESEARCH OR DEVELOPMENT

Not applicable.

BACKGROUND

1. Field

The following description relates to an ostomy leak proof protection bag that is used to cover the primary ostomy bag at all times for protection against leakage. For example, patients having undergone a colostomy where a portion of the colon or the intestine is removed will typically use an ostomy bag after the procedure. An ostomy bag is a prosthetic medical device that provides a means for the collection of waste from a surgically diverted biological system. An ostomy leak proof protection bag can be used to cover the ostomy bag for protective purposes.

2. Description of Related Art

A colostomy is a surgical procedure in which an opening or stoma is formed by drawing the healthy end of the large intestine or colon through an incision in the anterior abdominal wall and suturing it into place. This opening provides an alternative channel for feces and waste to leave the body. Use of the ostomy bag at the ostomy site allows for a collection device to collect body secretions.

The position of the stoma on the abdomen can occur at any location along the colon, but the most common position is the lower left side. The lower left side of the colon is the position where a majority of colon cancers occur. Other sections of the colon may also be used for placement of the stoma on the abdomen.

Ostomy pouching systems or bags usually consist of a collection pouch plastic bag and in some instances involve a mounting plate such as a flange. A collection pouch may also be attached mechanically or with an adhesive in an airtight seal. The selection of systems varies greatly and may be based on personal preference and lifestyle. The pouching system or ostomy bag allows the stoma to drain into a sealed collection pouch, while protecting the surrounding skin from contamination.

Ostomy pouching systems or bags may become compromised resulting in leakage of the bodies waste outside of the ostomy bag. Leakage of waste can occur as a result of many factors; such as external pressure on the bag, overflow of the waste material and improper placement of the ostomy bag as well as several others factors. Such compromising situations can have damaging effects on the patient such as depression, anxiety and isolation. Depression can occur as the individual is troubled by the events of leakage. Anxiety can occur as the individual becomes afraid that leakage can occur at anytime. Isolation can occur as the individual becomes embarrassed of these events of leakage and prefers to be isolated than to be in the company of others.

What results from these various circumstances of leakage is soiling to ones' clothing, foul odor, embarrassment, and change in activities. Providing a protective system such as an ostomy leak proof protection bag is a beneficial solution to guard against leakage and allow someone with an ostomy to continue to participate in their regular activities.

SUMMARY

This Summary is provided to introduce a selection of concepts in a simplified form that are further described below in the Detailed Description. This Summary is not intended to identify key features or essential features of the subject matter, nor is it intended to be used as an aid in determining the scope of the invention.

The following describe a leak proof protective system for covering an ostomy bag and flange. It is a one piece close ended system. The leak proof protective bag is a one piece attachment that has two components. The first component is an adhesive piece that covers over the ostomy bag flange or ostomy bag adhesive. This adhesive piece contains an absorbable attachment that soaks up the escaped waste and prevents further leakage. The second component is a soft, flexible plastic that is attached to the adhesive component that fully covers the ostomy bag allowing the ostomy bag to rest inside the protective bag. The second component is close ended to trap escaped fecal discharge from the ostomy bag. The outer layer of the flexible bag that faces the skin will have a breathable covering to prevent skin irritation. It will also have an air filter to release excess air and prevent inflation of the bag. The whole system covers over the ostomy bag.

As ostomy waste escapes the primary bag, it will enter into the secondary bag. One will be able to see through the clear bag that there is leakage and change both secondary system and primary system. Since this secondary support system covers the primary ostomy bag, disposal may include dropping the primary bag into the secondary bag without separating the two. This makes for easy disposal.

In an aspect, an ostomy bag system includes an ostomy bag having an ostomy bag adhesive and an ostomy bag pouch, and an ostomy protection bag cover having a cover adhesive and a cover pouch. The cover adhesive may enclose the ostomy bag adhesive and the protective cover pouch may enclose the ostomy bag pouch for additional sealing and protection. The ostomy bag pouch may overlap in position with the cover adhesive while being in front of the cover adhesive with respect to the patient's body.

In another aspect, a method of using an ostomy bag system includes securing an ostomy bag adhesive to a patient's body, securing a protective bag cover adhesive enclosing the ostomy bag adhesive to another position on the patient's body, and removing the ostomy bag system in a single step after use of the ostomy bag system. The one step removal process may include detaching the cover adhesive from the patient's body while grasping and pulling on the ostomy bag pouch for removing the entire system at once.

BRIEF DESCRIPTION OF THE DRAWINGS

The foregoing summary, as well as the following detailed description, will be better understood when read in conjunction with the appended drawings. For the purpose of illustration, certain examples of the present description are shown in the drawings. It should be understood, however, that the invention is not limited to the precise arrangements and instrumentalities shown. The accompanying drawings, which are incorporated in and constitute a part of this specification, illustrate an implementation of system, apparatuses, and methods consistent with the present description and, together with the description, serve to explain advantages and principles consistent with the invention.

Figure 1:
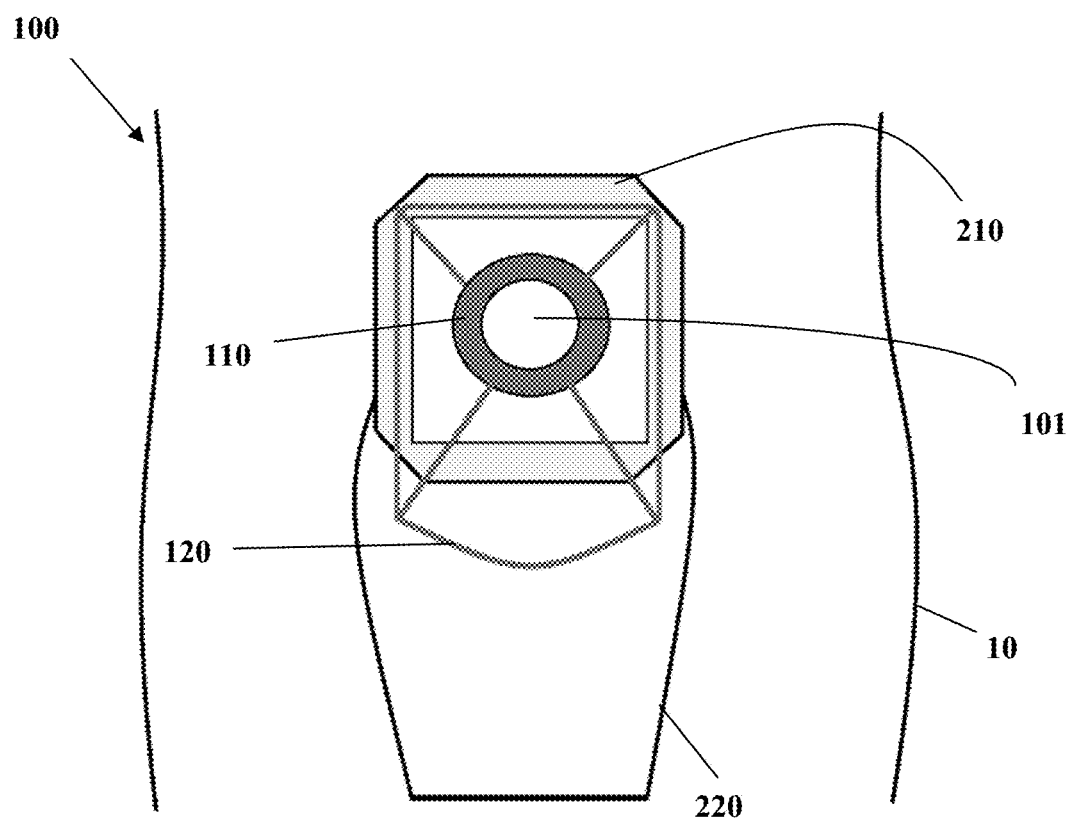
FIG. 1 is a diagram illustrating an example of an ostomy bag with an ostomy leak proof protection bag used for additional sealing and protection.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the systems, apparatuses and/or methods described herein will be suggested to those of ordinary skill in the art. Also, descriptions of well-known functions and constructions may be omitted for increased clarity and conciseness.

In addition, it is to be understood that the phraseology and terminology employed herein are for the purpose of description and should not be regarded as limiting. For example, the use of a singular term, such as, "a" is not intended as limiting of the number of items. Also the use of relational terms, such as but not limited to, "top," "bottom," "left," "right," "upper," "lower," "down," "up," "side," are used in the description for clarity and are not intended to limit the scope of the invention or the appended claims. Further, it should be understood that any one of the features can be used separately or in combination with other features. Other systems, methods, features, and advantages of the invention will be or become apparent to one with skill in the art upon examination of the detailed description. It is intended that all such additional systems, methods, features, and advantages be included within this description, be within the scope of the present invention, and be protected by the accompanying claims.

FIG. 1 is a diagram illustrating an example of an ostomy bag system 100 including an ostomy bag 110, 120 and an ostomy leak proof protection bag 210, 220. The ostomy bag 110, 120 includes an ostomy bag adhesive 110 and an ostomy bag pouch 120. The ostomy bag pouch 120 is configured to carry waste that exits from the ostomy site 101. The ostomy bag adhesive 101 is configured to secure the position of the ostomy bag 110, 120 with respect to the patient's body 10. Specifically, the ostomy bag adhesive may be secured adjacent to the ostomy site 101.

In this example, the ostomy bag adhesive 110 is in the shape of a circle with a circular opening and is secured around the ostomy site 101. The adhesive 110 is positioned on the interior face of the ostomy bag 110, 120 facing the patient's body for attaching directly thereto. The adhesive 110 has an opening extending through it for allowing a direct flow between the ostomy site 101, on which the ostomy bag 110, 120 is secured, and the ostomy bag pouch 120. Accordingly, as waste is excreted, it passes through the hole formed around the ostomy bag adhesive 110 and into the ostomy bag 120.

It should be appreciated that the surface of the adhesive 110 is the surface in closest proximity to the patient's body 10 as compared to the remaining components of the ostomy bag 110, 120. For example, the adhesive 110 may be the only portion of the ostomy bag 110, 120 that is directly contacting the patient's body 10. The ostomy bag pouch 120 may be spaced apart from the adhesive 110 and the patient's body 10. Further, while the ostomy bag adhesive 110 is circular in shape, the ostomy bag pouch 120 may have a rectangular-like shape. Referring to FIG. 1, the ostomy bag pouch 120 may be rectangular with rounded corners and edges, but it should be appreciated that the ostomy bag 110, 120 may have a variety of different shapes.

Still referring to FIG. 1, the ostomy bag system 100 further includes an ostomy leak proof protection bag 210, 220. The ostomy leak proof protection bag 210, 220 includes a cover adhesive 210 for securing the ostomy leak proof protection bag 210, 220 directly to the patient's body 10, and a cover pouch 220 for additional sealing and protection from leakage or compromise.

In this example, the cover adhesive 210 has a square shape with beveled corners but it should be appreciated that a variety of different shapes and sizes may be used. Also, the ratio of the area enclosed by the cover adhesive 210 is preferably at least 1.5:1 with respect to the area enclosed by the ostomy bag adhesive 110 such that the ostomy bag adhesive 110 is positioned inside the area enclosed by the cover adhesive 210. Because the interface between the patient's body 10 and the ostomy bag adhesive 110 is a position that is subject to leakage based on the quality of the ostomy bag adhesive 110, it is important that the cover adhesive 210 enclose this interface position. Accordingly, any leakage that occurs at the interface position would be captured by the cover pouch 220.

The cover pouch 220 may have a square or rounded shape that surrounds the entire ostomy bag 110, 120. Specifically, the ratio of the area enclosed by the cover pouch 220 is preferably at least 1.5:1 with respect to the area enclosed by the ostomy bag pouch 120 such that the ostomy bag pouch 120 is positioned inside the area enclosed by the cover pouch 220. Because the ostomy bag pouch 120 is subject to leakage based on the quality of the ostomy bag pouch 120, it is important that the cover pouch 220 encloses the ostomy bag pouch 120. Accordingly, any leakage that occurs at the ostomy bag pouch 120 would be captured by the cover pouch 220.

Figure 2:
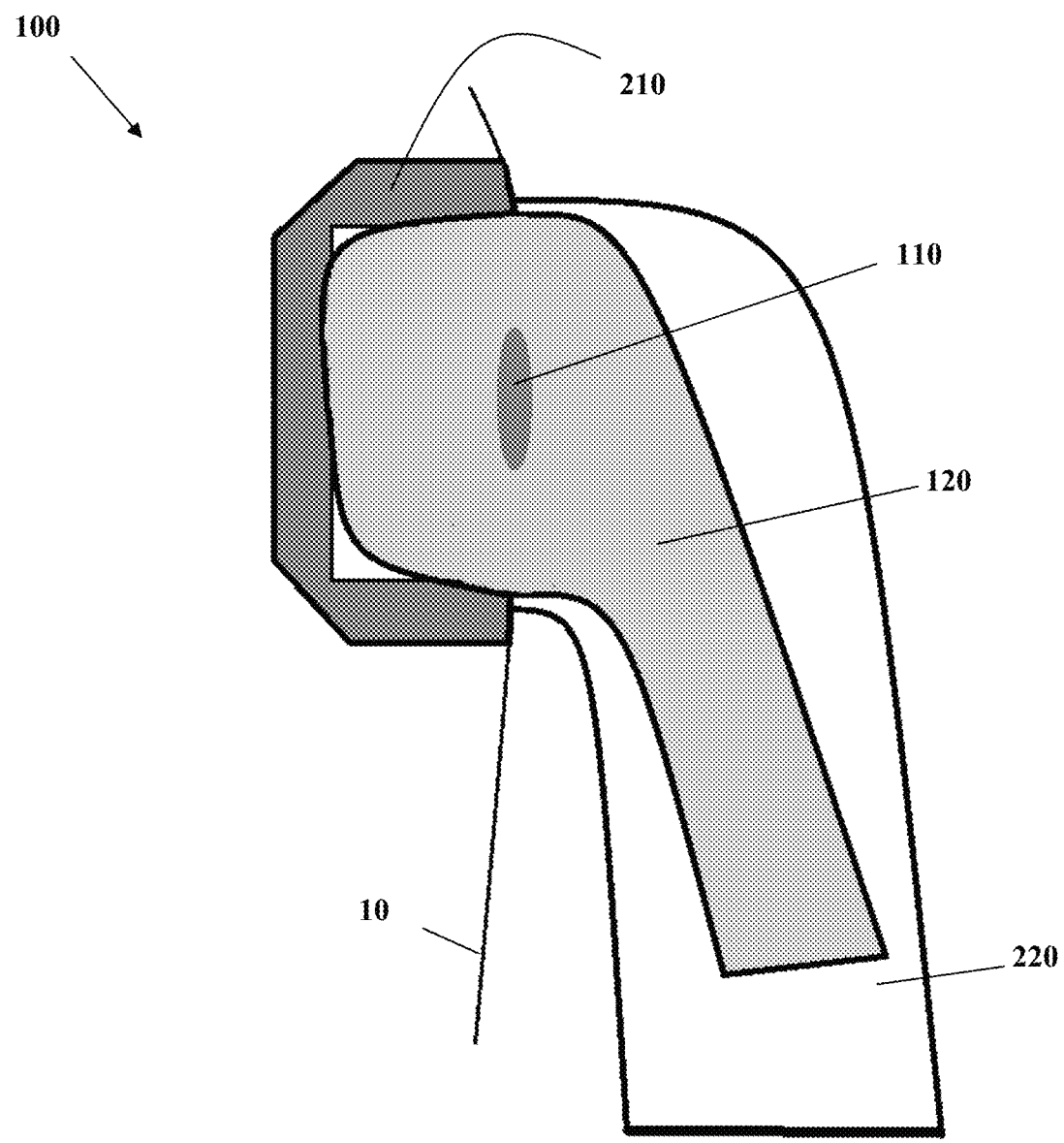
FIG. 2 is a side view illustrating an example of the ostomy bag with the ostomy leak proof protection bag used for additional sealing and protection.

Referring to FIG. 1 and FIG. 2 together, in a preferred example, the ostomy bag pouch 120 overlaps at least a portion of the surface of the cover adhesive 210. That is, the cover adhesive 210 is closer to the patient's body 10 than the ostomy bag pouch 120 because the cover adhesive 210 is directly adhered to the patient's body 10 while the ostomy bag pouch 120 may be separated from the patient's body. However, the ostomy bag pouch 120 may overlap the position of the cover adhesive 210 and be positioned in front of the cover adhesive 210 with respect to the patient's body 10.

This overlap allows for the easy and convenient removal of the entire ostomy bag system 100 in a one-step removal process. A patient can remove the entire ostomy bag system 100 by grasping the cover adhesive 210 together with the overlapping ostomy bag pouch 120 and remove the entire system 100 in a one step motion. This also ensures that any waste captured by the entire system 100 is safely and securely handled from the position on the patient's body 10 until disposal of the system 100.

Figure 3:
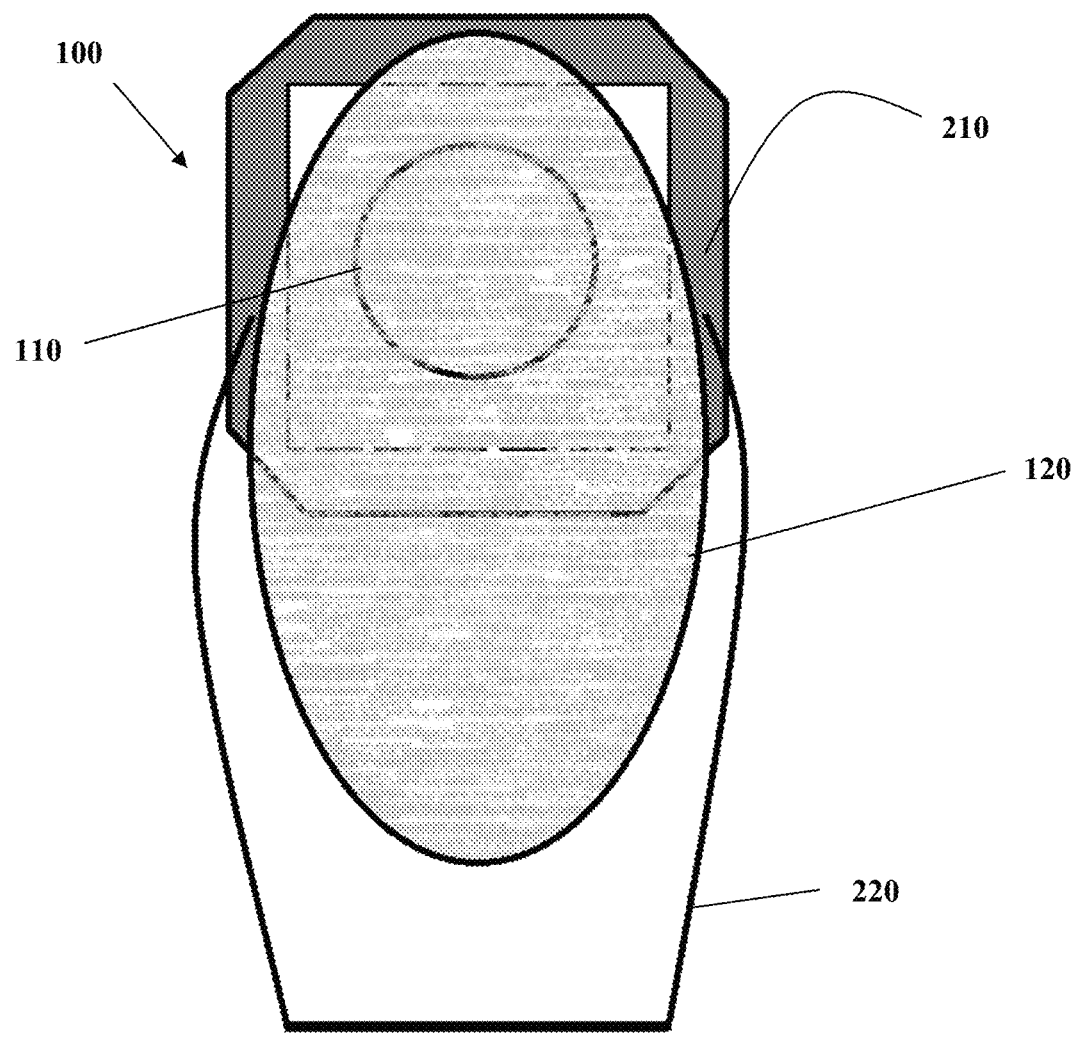
FIG. 3 is a diagram illustrating another example of an ostomy bag with an ostomy leak proof protection bag used for additional sealing and protection.

FIG. 3 is a diagram illustrating another example of the ostomy bag system 100. In this example, the ostomy bag pouch 120 may have an oval or circular shape that includes a rounded upper portion. The rounded upper portion of the ostomy bag pouch 120 may overlap with the upper edge of the cover adhesive 210 in at least one position. There may be a smaller position of overlap between the ostomy bag pouch 120 and the cover adhesive 210. However, the ostomy bag pouch 120 will overlap with at least a portion of every side of the cover adhesive 210.

Accordingly, the removal process described above will be applicable to the example illustrated in FIG. 3.

The materials used for the ostomy leak proof protection bag 210, 220 may include flexible, soft, and transparent plastic material for the cover pouch 220 and an adhesive material for the cover adhesive 210. The cover pouch 220 may loosely cover the ostomy pouch 120 and is flexible to allow for easy portability prior to use and during disposal. The cover pouch 220 is also transparent to allow a user to detect when replacement of the system 100 is required and when compromise of the primary bag has occurred.

The cover pouch 220 may also include an additional outer layer of material that faces the skin of the patient that includes a breathable covering to prevent skin irritation to the patient when the pouch 220 comes in contact with the patient. Additionally, the cover pouch 220 may include an air filter in a variety of positions, such as at an upper portion, to release excess air and prevent inflation of the bag while reducing any additional risk of leakage. The cover adhesive 210 may also include an additional buffer ring material at the adhesive end to absorb watery fecal discharge and prevent further leakage.

Figure 4:
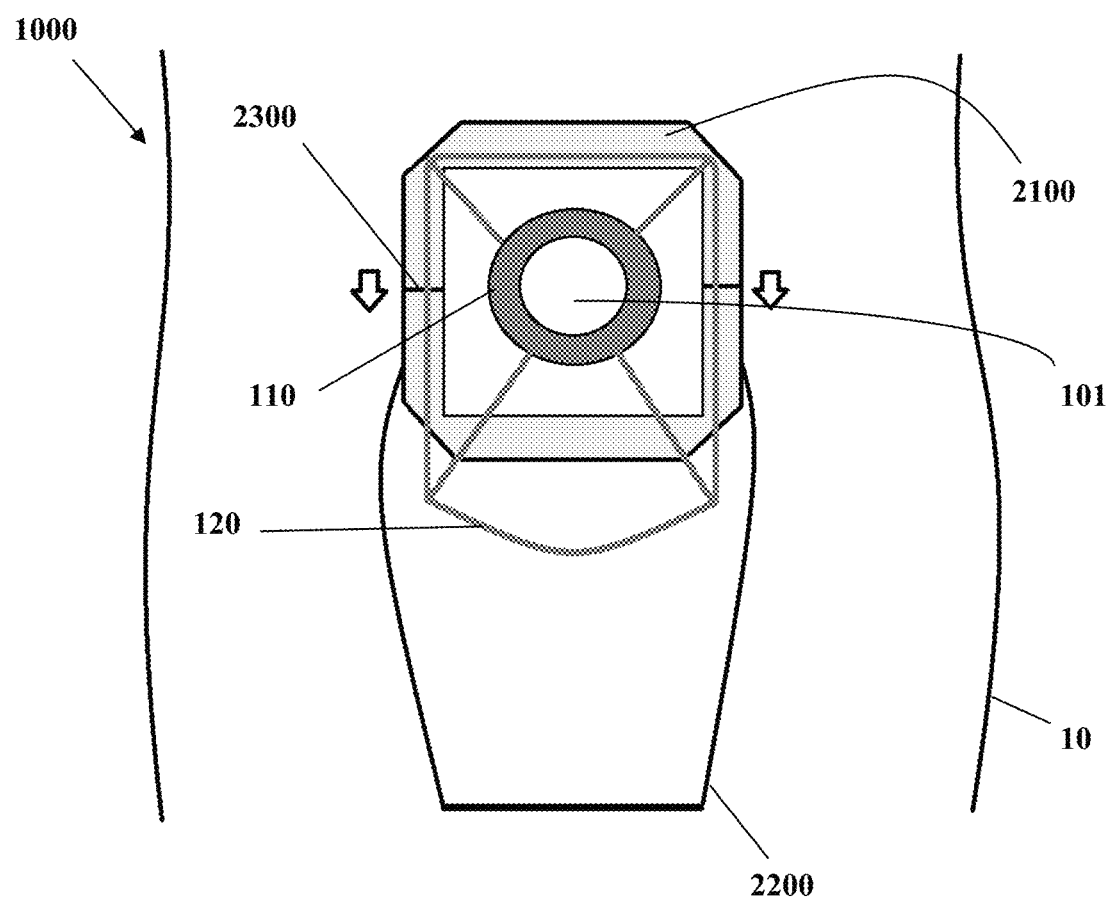
FIG. 4 is a diagram illustrating another example of an ostomy leak proof protection bag used having a hinge element.

FIG. 4 is a diagram illustrating another example of an ostomy bag system 1000 including the ostomy bag 110, 120 described above in reference to FIGS. 1-3, and another example of an ostomy leak proof protection bag 2100, 2200, 2300. The ostomy bag 110, 120 includes an ostomy bag adhesive 110 and an ostomy bag pouch 120, as was previously described above. The ostomy leak proof protection bag 2100, 2200, 2300 includes a cover adhesive 2100 for securing the ostomy leak proof protection bag 2100, 2200, 2300 directly to the patient's body 10, and a cover pouch 2200 for additional sealing and protection from leakage or compromise.

Figure 5:
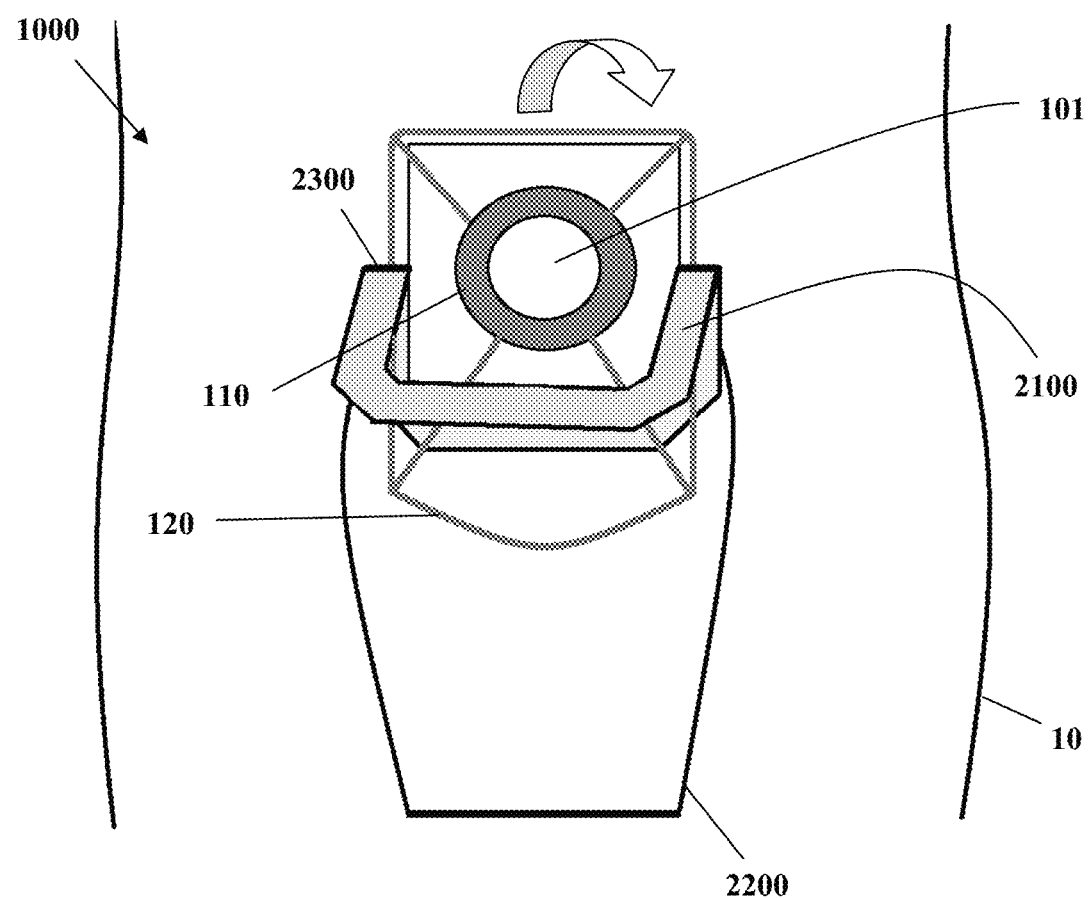
FIG. 5 is a diagram illustrating the ostomy leak proof protection bag having the hinge element in an open configuration.

In this example, the ostomy leak proof protection bag 2100, 2200, 2300 further includes a hinge element 2300 that is positioned on the cover adhesive 2100. For example, the ostomy leak proof protection bag 2100, 2200, 2300 may include two hinges 2300 that are positioned on opposite side members of the square shaped cover adhesive 2100. Referring now to FIG. 5, the hinge elements 2300 allow the ostomy leak proof protection bag 2100, 2200, 2300 to open partially so that an upper portion of the cover adhesive 2100 is detached from the patient's body 10. This allows the easy and clean removal and replacement of the ostomy bag 110, 120. Typically, the removal of an ostomy bag 110, 120 having a cover may require the removal of the entire system. In this example, only part of the ostomy bag system 1000 is removed—the ostomy bag 110, 120. The system 1000 is generally maintained in position while replacement of only the ostomy bag 110, 120 may be completed.

Figure 6:
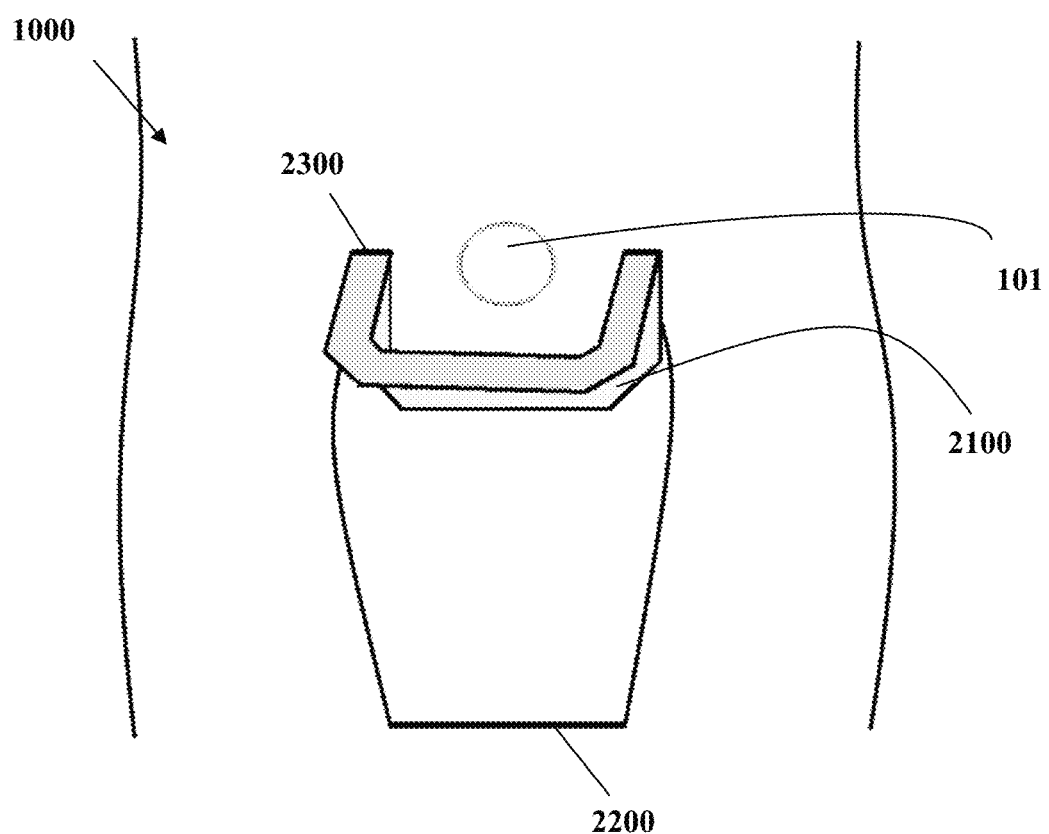
FIG. 6 is a diagram illustrating the ostomy leak proof protection bag having the hinge element with the ostomy bag removed for replacement.

Referring now to FIG. 6, the ostomy leak proof protection bag 2100, 2200, 2300 with the ostomy bag 110, 120 removed for replacement is illustrated. In this example, the leak proof protection bag 2100, 2200, 2300 includes the hinge element 2300 and is shown in the open configuration with the ostomy bag 110, 120 removed. The ostomy site 101 is also easily accessible in response to the leak proof protection bag 2100, 2200, 2300 being in the open configuration. This allows for cleaning of the ostomy site 101 in addition to replacement of the ostomy bag 110, 120.

While the leak proof protection bag 2100, 2200, 2300 of FIGS. 4-6 is illustrated with hinge elements 2300 positioned on opposite ends of its side members, other structures allowing an open configuration can be used. For example, instead of hinge elements 2300 positioned on the cover adhesive 2100, the cover adhesive 2100 may be constructed using two half square wire frames that are covered by the adhesive and separated at the position shown at the hinge in FIGS. 4-6. That is, the upper portion of the cover adhesive 2100 is supported by a first wire frame that is underneath or embedded within the cover adhesive 2100, and the bottom portion of the cover adhesive 2100 is supported by a separate, second wire frame that is underneath or embedded within the cover adhesive. This allows the cover adhesive to bend at the bending point which is formed between the two frames, and provides a leak proof protection bag 2100, 2200 that does not have hinge elements 2300 but still allows the opening and closing of the leak proof protection bag 2100, 2200, as illustrated in FIG. 6.

A method of using the ostomy bag system 1000 including the ostomy bag 110, 120 and ostomy leak proof protection bag 2100, 2200, 2300 of FIGS. 4-6 may include placing an ostomy bag 110, 120 on a patient's body 10, placing an ostomy leak proof protection bag 2100, 2200, 2300 over the ostomy bag 110, 120 by placing the ostomy bag pouch 120 inside the cover bag 2200 and sticking the cover adhesive 2100 on the patient's body 10 in a region around the ostomy bag adhesive 110, detaching an upper portion of the cover adhesive 2100 from the patient's body 10, opening the cover adhesive 2100 downward and partially so that the ostomy bag 110, 120 is exposed, removing and replacing the ostomy bag 110, 120, and reattaching the upper portion of the cover adhesive 2100 to the patient's body 10 so that the replaced ostomy bag 110, 120 is covered.

A person of ordinary skill in the art will recognize that the described examples are not limited to any particular size. Further a person of ordinary skill in the art will recognize that the components of the ostomy bag system 100 are not limited to any type of material. A person of ordinary skill in the art will recognize that diameters, types and thicknesses of preferred materials can be utilized when taking into consideration safety, comfort, security, and sealing. A number of manufacturing techniques may be used for any component of the ostomy bag system 100.

It will be appreciated by those skilled in the art that changes could be made to the embodiments described above without departing from the broad inventive concept thereof. It is understood, therefore, that the invention disclosed herein is not limited to the particular embodiments disclosed, and is intended to cover modifications within the spirit and scope of the present invention.

What is claimed is:

1. An ostomy bag system, comprising:
an ostomy bag comprising: an ostomy bag adhesive having a first opening; and an ostomy bag pouch having a second opening aligned with the first opening; the ostomy bag adhesive configured to adhere the ostomy bag to a patient's body; and
an ostomy protection bag cover comprising:
a cover adhesive having a third opening;
a cover pouch having a fourth opening aligned with the third opening; and
two hinge elements positioned on opposite sides of the cover adhesive configured for opening the ostomy protection bag cover and accessing the ostomy bag without completely removing the ostomy protection bag cover;
wherein the third opening is surrounded by the two hinge elements and configured for providing access to the ostomy bag between a patient's skin and an inner surface of the ostomy protection bag cover;
wherein the cover adhesive is configured to at least partially enclose the ostomy bag adhesive, and the cover pouch encloses the ostomy bag pouch such that the ostomy protection bag cover is configured to provide sealing and protection from leaks of the ostomy bag within the ostomy protection bag cover, and
wherein, in use, the ostomy bag pouch and the ostomy bag adhesive are configured to be overlapped by the cover adhesive and the inner surface of the cover pouch, such that the first, second, third, and fourth openings are substantially aligned with each other, such that the ostomy bag and the ostomy protection bag cover are configured to be removed simultaneously by grasping the cover adhesive together with the overlapped ostomy bag pouch,
wherein the cover adhesive has a square shape with beveled corners,
wherein the cover pouch is formed of a flexible and transparent plastic material,
wherein a boundary of the cover adhesive comprises:
a top edge extending from a first beveled corner of the cover adhesive to a second beveled corner of the cover adhesive,
a side edge extending from the first beveled corner of the cover adhesive to a third beveled corner of the cover adhesive, and
another side edge extending from the second beveled corner of the cover adhesive to a fourth beveled corner of the cover adhesive, and
wherein, in use, the at least a portion of the top, side, and another edge of the cover adhesive is directly adhered to the patient's body while covering the upper portion of the ostomy bag pouch.

2. The ostomy bag system of claim 1, wherein the ostomy bag adhesive is circular in shape with a circular opening.

3. The ostomy bag system of claim 1, wherein a ratio of an area enclosed by the cover pouch is at least 1.5:1 with respect to an area enclosed by the ostomy bag pouch.

4. The ostomy bag system of claim 1, wherein the ostomy protection bag cover further comprises an outer layer of material on a side facing the patient's body which is formed of breathable material to prevent skin irritation.

5. The ostomy bag system of claim 1, further comprising an air filter provided in the cover pouch and configured to release excess air and prevent inflation.

6. A method of using an ostomy bag system, comprising:
providing an ostomy bag system, comprising:
an ostomy bag comprising: an ostomy bag adhesive having a first opening; and an ostomy bag pouch having a second opening aligned with the first opening; the ostomy bag adhesive configured to adhere the ostomy bag to a patient's body; and
an ostomy protection bag cover comprising:
a cover adhesive having a third opening;
a cover pouch having a fourth opening aligned with the third opening; and
two hinge elements positioned on opposite sides of the cover adhesive configured for opening the ostomy protection bag cover and accessing the ostomy bag without completely removing the ostomy protection bag cover,
wherein the third opening is surrounded by the two hinge elements and configured for providing access to the ostomy bag between a patient's skin and an inner surface of the ostomy protection bag cover;
wherein the cover adhesive is configured to at least partially enclose the ostomy bag adhesive, and the cover pouch encloses the ostomy bag pouch such that the ostomy protection bag cover is configured to provide sealing and protection from leaks of the ostomy bag within the ostomy protection bag cover, and
wherein, in use, the ostomy bag pouch and the ostomy bag adhesive are configured to be overlapped by the cover adhesive and the inner surface of the cover pouch, such that the first, second, third, and fourth openings are substantially aligned with each other, such that the ostomy bag and the ostomy protection bag cover are configured to be removed simultaneously by grasping the cover adhesive together with the overlapped ostomy bag pouch,
wherein the cover adhesive has a square shape with beveled corners,
wherein the cover pouch is formed of a flexible and transparent plastic material;
wherein a boundary of the cover adhesive comprises:
a top edge extending from a first beveled corner of the cover adhesive to a second beveled corner of the cover adhesive,
a side edge extending from the first beveled corner of the cover adhesive to a third beveled corner of the cover adhesive, and
another side edge extending from the second beveled corner of the cover adhesive to a fourth beveled corner of the cover adhesive,
securing the ostomy bag adhesive to a position on the patient's body;
securing the at least a portion of the cover adhesive to another position on the patient's body;
wherein, in use, the at least a portion of the top, side, and another edge of the cover adhesive is directly adhered to the another portion of the patient's body while covering at least a portion the upper portion of the ostomy bag pouch, and
removing the ostomy bag system in a single step after use of the ostomy bag system by detaching the cover adhesive from the patient's body while grasping and pulling on the ostomy bag pouch for removing the entire system at once.

7. The method of claim 6, wherein the ostomy bag adhesive is circular in shape with a circular opening.

8. The method of claim 6, wherein the cover adhesive has a square shape with beveled corners.

9. The method of claim 6, wherein a ratio of an area enclosed by the cover pouch is at least 1.5:1 with respect to an area enclosed by the ostomy bag pouch.

10. The method of claim 6, wherein the ostomy protection bag cover wherein the pouch cover is formed of flexible and transparent plastic material.

11. The method of claim 6, wherein the ostomy protection bag cover further comprises an outer layer of material on a side facing the patient's body which is formed of breathable material configured to prevent skin irritation.

12. The method of claim 6, wherein the ostomy bag system further comprises an air filter provided in the cover pouch and configured to release excess air and prevent inflation.

13. The method of claim 6, wherein the ostomy bag system further comprises a first wire frame that is underneath or embedded within an upper portion of the cover adhesive and a second wire frame that is underneath or embedded within a lower portion of the cover adhesive.

14. An ostomy bag system, comprising:
- an ostomy bag comprising an ostomy bag adhesive having a first opening; and an ostomy bag pouch having a second opening aligned with the first opening; the ostomy bag adhesive configured to adhere the ostomy bag to a patient's body; and
- an ostomy protection bag cover comprising:
  - a cover adhesive having a third opening;
  - a cover pouch having a fourth opening aligned with the third opening;
  - a first wire frame that is underneath or embedded within an upper portion of the cover adhesive;
  - a second wire frame that is underneath or embedded within a lower portion of the cover adhesive; and
  - two hinge elements connecting opposite ends of the first and second wire frames and positioned on opposite sides of the cover adhesive configured; the two hinge elements and first and second wire frames configured for opening the ostomy protection bag cover and accessing the ostomy bag without completely removing the ostomy protection bag cover; and wherein the third opening is surrounded by the first and second wire frames and the two hinge elements, and configured for providing access to the ostomy bag between a patient's skin and an inner surface of the ostomy protection bag cover;

wherein the cover adhesive is configured to at least partially enclose the ostomy bag adhesive, and the cover pouch is configured to enclose the ostomy bag pouch, such that the ostomy protection bag cover is configured to provide sealing and protection from leaks of the ostomy bag within the ostomy protection bag cover, wherein, in use, the ostomy bag pouch and the ostomy bag adhesive are configured to be overlapped by the cover adhesive and the inner surface of the cover pouch, such that the first, second, third, and fourth openings are substantially aligned with each other, and such that the ostomy bag and the ostomy protection bag cover are configured to be removed simultaneously by grasping the cover adhesive together with the overlapped ostomy bag pouch, wherein the cover adhesive has a square shape with beveled corners, wherein the cover pouch is formed of a flexible and transparent plastic material, wherein a boundary of the cover adhesive comprises:
- a top edge extending from a first beveled corner of the cover adhesive to a second beveled corner of the cover adhesive,
- a side edge extending from the first beveled corner of the cover adhesive to a third beveled corner of the cover adhesive, and
- another side edge extending from the second beveled corner of the cover adhesive to a fourth beveled corner of the cover adhesive, wherein, in use, the at least a portion of the top, side, and another edge of the cover adhesive is directly adhered to the patient's body while covering the upper portion of the ostomy bag pouch.

* * * * *